United States Patent [19]

Box

[11] Patent Number: 4,908,097

[45] Date of Patent: Mar. 13, 1990

[54] MODIFIED CELLULOSIC FIBERS

[75] Inventor: Larry Box, Glen Mills, Pa.

[73] Assignee: Scott Paper Company, Philadelphia, Pa.

[21] Appl. No.: 265,359

[22] Filed: Oct. 26, 1988

Related U.S. Application Data

[63] Continuation of Ser. No. 40,960, Apr. 21, 1987, abandoned, which is a continuation-in-part of Ser. No. 763,301, Aug. 2, 1985, abandoned, which is a continuation-in-part of Ser. No. 576,828, Feb. 3, 1984, abandoned.

[51] Int. Cl.$^4$ .......................... D21C 9/00; D21C 9/153
[52] U.S. Cl. ............................................. 162/9; 8/194; 162/65; 162/72; 162/157.6; 162/182; 536/56
[58] Field of Search .................. 162/157.6, 175, 9, 72, 162/182, 65; 8/194; 536/56

[56] References Cited

U.S. PATENT DOCUMENTS

| | | | |
|---|---|---|---|
| 2,338,681 | 1/1944 | Bock et al. | 536/56 |
| 3,029,232 | 4/1962 | Bikales | 536/56 |
| 3,135,738 | 6/1964 | Cushing | 162/175 |
| 3,440,135 | 4/1969 | Chung | 162/157.6 |
| 3,700,549 | 10/1972 | Croon et al. | 162/157.6 |
| 3,926,555 | 12/1975 | Reine et al. | 8/194 |
| 4,248,595 | 2/1981 | Lask et al. | 8/194 |
| 4,431,481 | 2/1984 | Drach et al. | 162/9 |
| 4,505,775 | 3/1985 | Harding et al. | 162/9 |

FOREIGN PATENT DOCUMENTS

818412 8/1959 United Kingdom ................. 536/56

OTHER PUBLICATIONS

Frick et al., "Chemical Modification of Cotton by Reaction with Activated Olefinic Compounds", Textile Research Journal; vol. XXVII, No. 2, Feb. 1957, pp. 92-99.

Casey, *Pulp and Paper*, 2nd ed. (1960), vol. I, pp. 10-13, 244, 245, 516, 517.

*Primary Examiner*—Peter Chin
*Attorney, Agent, or Firm*—John A. Weygandt; John W. Kane, Jr.

[57] ABSTRACT

Disclosed are modified cellulosic fibers comprising the reaction product of linear, water-wettable polysaccharides with N,N'-methylenebisacrylamide and methods of making same. The materials are useful in the preparation of products characterized by their increased bulk and absorbency.

11 Claims, No Drawings

MODIFIED CELLULOSIC FIBERS

RELATED APPLICATIONS

This application is a continuation of application Ser. No. 07/040,960, filed Apr. 21, 1987 now abandoned which is a continuation in-part of Ser. No. 06/763,301 filed Aug. 2, 1985 for "Modified Cellulosic Fibers" which in turn is a continuation-in-part of Ser. No. 06/576828 filed Feb. 3, 1984 for "Modified Polysaccharide Materials."

BACKGROUND OF THE INVENTION

FIELD OF THE INVENTION

This invention relates to the modification of polysaccharide materials by treatment with an amide. When such polysaccharide materials are cellulosic fibers, webs comprising such modified fibers and untreated fibers exhibit increased bulk and absorbency.

DEFINITIONS

For purposes of this invention, a "water-wettable polysaccharide" is one which is either insoluble in water or capable of absorbing water and being swollen thereby.

As used herein, the term "cellulosic fibers" refers to fibers comprising cellulose, a linear, water-wettable polysaccharide, whether existing as a single constituent in a larger natural aggregate such as wood pulp, bagasse and cotton linters, or as a derivative of the natural aggregate such as alpha pulp or viscose rayon.

The term "fines" means cellulosic fibers less than 2 mm in length.

The term "consistency" means the weight of fibers in a pulp suspension or wetted fibrous batt or web usually expressed as a percentage. For example, ten pounds of oven dry fibers in one hundred pounds of a mixture of water and fibers would be a suspension of 10% consistency.

SUMMARY OF THE INVENTION

The present invention relates to the preparation of novel cellulosic fibers comprising the reaction product of untreated cellulosic fibers, preferably wood pulp, with N,N'-methylenebisacrylamide. The reaction is carried out in the presence of alkali by combining the N,N'-methylenebisacrylamide with a high consistency aqueous mixture of the cellulosic fibers or by applying it in the form of a solution to a batt or web of cellulosic fibers. The consistency of said mixture should be at least 10% in order to effect a satisfactory efficiency of the reaction. Optimally, mixtures are of 20-45% consistency. Batts or webs are generally of greater than 45% consistency. By following the teachings of the present invention, efficiencies, (as measured by nitrogen assays of washed fibers) of from 40% to greater than 70% can be obtained. The reaction is preferably allowed to proceed for several days at ambient temperature, for example 25° C., or for a day at a slightly elevated temperature, for example 35° C. While the reaction can be accelerated and brought to completion within hours or minutes at temperatures above 50° C., provided that the temperature of the aqueous medium remains below its boiling point, the desired modification of the fibers, as measured by increased bulk and absorbency of the resulting fibrous web, is not as great as that obtained at lower temperatures. As will be appreciated by those familiar with the prior art pertaining to treatment of cellulose with acrylamides, this preference for ambient temperatures represents a teaching in the direction opposite of that taught by the prior art. It represents not merely an effort to protect the cellulose from degradation in hot alkali but the deliberate favoring of a reaction, not fully understood by the present inventor, which produces unexpected and heretofore unknown benefits in terms of increased bulk and absorbency of the resulting fibrous web. Free radical initiators should be excluded from the reaction medium, possibly because they neutralize the reactive sites on N,N'-methylenebisacrylamide for carbamoylethylation, namely, the double bonds. Air can likewise have a poisoning effect on the desired reaction. After the N,N'-methylenebisacrylamide and cellulosic fibers are combined, it is necessary to exclude air from the materials while the reaction is taking place. In order for the desired reaction to proceed quiescent, non-aerated conditions which do not permit the introduction of air, should be employed. While obviously some air is generally dissolved in water and may be entrapped in the interstices of a batt of fibers, if the reactants are freely exposed to ambient air, virtually no N,N'-methylenebisacrylamide will be found to have reacted with the cellulosic fibers. It will therefore be apparent that conditions or actions which cause air to be entrapped or entrained in the medium, such as application by spraying must be remedied by subsequent purging of air from the medium. Applying the N,N'-methylenebisacrylamide by compressive means, such as in a high consistency refiner or by immersion or flooding, as illustrated in Example 7 herein, is preferred.

DESCRIPTION OF THE PREFERRED EMBODIMENTS

In accordance with the method of the present invention, the reaction is carried out in a high consistency aqueous mixture of cellulosic fibers or by applying the N,N'-methylenebisacrylamide in solution to a batt or web of cellulosic fibers, for example pulp lap. The amount of N,N'-methylenebisacrylamide to be dissolved in the aqueous alkaline medium with the cellulosic fibrous material should be sufficient to impart the desired increase in bulk and absorbency. Above about 5% N,N'-methylenebisacrylamide by dry weight of the fibers there is no additional effect on the fibers. Insufficient N,N'-methylenebisacrylamide, generally below 0.2%, will produce no perceptible change in the bulk or total water absorption of a web of the fibers, although any measurable amount of N,N'-methylenebisacrylamide produces a measurable increase in absorbency i.e. the rate of absorption. In practice using sufficient N,N'-methylenebisacrylamide to cause from about 0.5 to 2% by dry weight of the fibers to react with the fibers produces a level of modification sufficient for commercial applications.

While a certain amount of alkali is necessary for the reaction of the invention, it has been found that it is not necessary to apply alkali with the N,N'-methylenebisacrylamide or to combine them prior to application. It may be applied either before or after the N,N'-methylenebisacrylamide as well as with it, in an amount equivalent in alkali strength or hydroxyl ($OH^-$) ion contribution to up to ten parts by weight sodium hydroxide to fiber, and preferably 2 to 3 parts by weight. As will be appreciated by one of ordinary skill in the art, sodium hydroxide is the most convenient source of alkalinity in a pulp mill, but other sources such as potassium hydroxide and trisodium phosphate ($Na_3PO_4$) can be substituted. Preferably, the alkali is applied as a dilute solution, e.g. 1% of sodium hydroxide, by spraying or dipping as will be more fully described in the examples which follow.

The novel modified fibers of this invention may be used in combination with conventional papermaking fibers to produce webs which exhibit increased bulk and absorbency. The modified fibers of the present invention improve the bulk and absorbency of the base web in direct proportion to the percentage of modified fiber in the blend. Alternatively, blending can permit a reduction in basis weight while retaining bulk and absorbency. By way of illustration, in a web containing 30% modified fiber, basis weight was reduced by 25% without loss of bulk and absorbency as compared with a web without modified fibers of the present invention. Another utility of the fibers of the invention is as a replacement for any of the known super absorbent fibers such as the "super slurper" fibers for use in a variety of absorbent products such as diapers, sanitary napkins, hospital dressings and the like. Unlike the typical super-absorbent fibers which characteristically have a gelatinous or "slimy" feel when wet, the fibers made in accordance with the present invention retain their wood pulp-like feel to the touch. A further advantage of the present invention is that the modified fibers exhibit wet resilience. That is to say, the fibers retain their bulk when wet which is important in many absorbent products, such as diapers, where the shape and volume of the product when wet plays an important part in the function of the product, e.g: in retaining fit and wicking. Previous inventors have attempted to achieve these same properties, but found it necessary to employ rather elaborate and severe chemical conditions to achieve only some of these properties. For example, Lask, U.S. Pat. No. 4,248,595 granted Feb. 3, 1981, discloses a method to produce "swellable carboxyalkylcelluloses" from a two-part chemical system comprising first a carboxyalkyl etherifying agent and second a crosslinking agent in an aqueous alkaline medium. Furthermore, a very much larger proportion of the etherifying agent and alkali based on the weight of fiber is required by the process of Lask relative to N,N'-methylenebisacrylamide, which is employed by Lask solely to crosslink the etherifying agent. In the present invention no such etherifying agent is employed, a much lower alkali concentration is required and the reaction chemistry of N,N'-methylenebisacrylamide resembles that of the carbamoylethylation class of reactions as opposed to crosslinking as described by Lask. However, inasmuch as there is an abundance of non-cellulosic substances present in typical sources of cellulosic fibers, e.g., wood pulp, amylase starch and regenerated cellulose, some other reaction may be responsible for the modification produced in accordance with the present invention.

The present inventor is unaware of any disclosure in the prior art which would suggest such results from N,N'-methylenebisacrylamide Indeed, several other amides and acrylates were tried but did not produce clear improvements in absorbency and bulk. These compounds include Acrylamide
N-Methylolacrylamide
Bisacrylamide Glyoxal
N-Isopropylacrylamide
N-N Dimethylamino ethyl methacrylate
Triallylcyanurate
Glycidyl Acrylate
Acrylic Acid The remarkable results attained with N,N'-methylenebisacrylamide in accordance with the present invention are especially surprising in view of the prior art. The alkali concentrations employed in the present invention are relatively low. In such alkali media of relatively low concentration, the base catalyzed reaction of cellulose with acrylamide has long been believed to produce carbamoylethylcellulose. U.S. Pat. No. 2,338,681 granted to Bock et al Jan. 4, 1944. There is no suggestion in the prior art that carbamoylethylcellulose provides greater bulk and absorbency to webs. Indeed, the pertinent prior art suggests that such forms of cellulose are soluble in water when sufficiently modified with acrylamide. Bikales et al, U.S. Pat. No. 3,029,232 granted Apr. 10, 1962. Bikales et al observed in Example 8 that paper made from cellulose treated with N-n-propylacrylamide is stronger than from untreated pulp. However, they reported no change in absorbency of the fibers. Applicant's fibers, in contrast, form weaker webs having greater absorbency and bulk. It is to be concluded, therefore, that the reaction product of the present invention has a chemical composition different from or comprises something in addition to carbamoylethylated cellulose as understood by the prior art. Without wishing to be bound by theory, the present inventor believes that the high pulp consistencies employed in accordance with the present invention and the absence of a continuous aqueous phase tend to constrain the N,N'-methylenebisacrylamide to react at the surface of the fiber. These features are in sharp contrast to Bikales, et al. whose teachings suggest a continuous aqueous phase voluminous enough to keep the high concentration of salt in solution and to form intimate contact between the fibers and salt solution.

Treatment of wood pulp fibers treated in accordance with the present invention results in extended hydrophilicity, increased brightness and receptivity to ink, and in fibers which are more readily debonded thus resulting in bulkier, softer paper than the same fiber in the untreated form. There is at the same time no perceptible change in the structural appearance of the fibers. These improved properties are retained by the fibers when subjected to typical stress to which pulp fibers are subjected, for example, boiling water, moderately strong acid and alkali, and bleaching chemicals. Bleaching with chlorine, chlorine dioxide, hydrogen peroxide, ozone and combinations of such bleaching steps will not undo the fiber modification. This persistence of the structural integrity of the fibers (as well as the improved properties) further distinguishes the fibers resulting from the process of the present invention from those carbamoylethylated cellulose fibers of the prior art which are soluble in water. See U.S. Pat. No. 3,029,232, Column 5, lines 14-15.

The method of the present invention is not limited to any particular type of cellulosic fiber and has been successfully employed on a wide variety of wood pulps, both chemical and mechanical, hard wood and softwood, bagasse, secondary (recovered waste paper) and rayon staple fibers. In one embodiment of the present invention, the N,N'-methylenebisacrylamide reagent is combined with the sodium hydroxide used for the second extraction stage during a bleaching sequence such as CEHED, chlorine-alkali extraction—hypochlorite-alkali extraction—chlorine dioxide or CEDED, chlorine-alkali extraction—chlorine dioxide-alkali extraction—chlorine dioxide. The temperature e.g. 60° C., and duration, typically one hour, of such a stage are sufficient for the modification reaction to be completed. The final bleach stage (chlorine dioxide) serves as a neutralization and washing step.

The present invention provides overall improvement in the wood pulps produced by "high yield" or mechanical pulping processes, e.g. thermomechanical and refiner mechanical pulps which are characterized in having larger hemicellulose and carbohydrate contents than chemical pulp. Since, as previously mentioned, the modification imparted to cellulosic fibers by N,N'-methylenebisacrylamide survives delignification treatments, the aforementioned treatment of "high yield" or mechanical pulps can be advantageously combined with a delignification step, either prior to or subsequent to application of the method of the present invention.

Mechanical pulps are desirable in that they are produced in high yield, but have found limited use in absorbent paper products due to their rigid structure. In the past, attempts have been made to produce fibers which have enhanced flexibility compared to groundwood, refiner mechanical pulp, thermomechanical pulp, chemi-refiner and chemi-thermomechanical pulp though delignification. Unfortunately, total or partial delignification produces pulps with reduced bulk. The latter phenomenon is disadvantageous when the end-use of the fiber is in absorbent products.

In accordance with the present invention mechanical fibers can be made flexible while maintaining or improving their bulk characteristics. These fibers are subjected to, for example, ozonization whereby at least partial delignification is achieved, resulting in low bulk high-bonding fibers, which upon subsequent treatment in accordance with the present invention results in a pulp with high brightness, bulk and flexibility. Alternatively, the method of the present invention can be applied prior to the delignification stage. In this connection, it is to be noted that fibers treated in accordance with the present invention exhibit sharp reductions in bleach chemical demand.

A further advantage of the present invention is that when short cellulosic fibers, hereinafter called fines, are modified in accordance with the present invention, they become non-binding and dispersible. This feature has significant economic implications. In particular, it permits the use of pulp furnishes containing a high proportion of fines without the normal difficulties. Wood fines, an assortment of particulate wood products which pass through a 75 micron opening, exhibit rather noticeable adhesive properties uncommon to regular wood fibers. Consequently, when isolated and dried they form a dense agglomerated structure which resists being dispersed in water. In this agglomerated state, fines interfere with both the manufacture of absorbent papers and their product qualities. When fines are treated in accordance with the present invention, they become soft and dispersible in water after drying. By way of illustration, a stone ground wood pulp containing 23% fines, when formed into a mat from an aqueous dispersion, dried into a rough textured non-dispersible mass. When the same pulp was treated in accordance with the method of present invention with 2.5% N,N'-methylenebisacrylamide based on dry pulp weight, neutralized and dried, the treated fines were found to be soft and dispersible.

It can be appreciated by one of ordinary skill in the art to which the present invention pertains that a large number of variations may be effected in reacting the cellulosic fibrous material with N,N'-methylenebisacrylamide in accordance with the reaction procedures described above, without materially departing from the scope and spirit of the invention. The following examples will more fully illustrate the embodiments of this invention. In the examples all temperatures are in degrees Celsius. The basis weight of webs is expressed in grams per square meter. "Wet pick-up" is expressed as a percent by weight of the dry fibers to which the solution is applied. The abbreviation "TWA" stands for "total water absorbed" and is determined on a gram for gram basis, e.g. a TWA of 2 means 2 grams of water were absorbed for each gram of fiber. The ratio of bulk to basis weight is a means of comparing the bulk of webs of different basis weight. A larger ratio indicates greater bulkiness (lesser density) and is regarded as an improvement in sanitary tissue. This ratio and TWA are the principal criteria for measuring the improvements produced in accordance with the present invention. "Breaking length" is the estimated length at which the web would break under its own weight. It is derived from a measurement of the tensile strength of the web and related to its basis weight. While non-empirical, it is useful in comparing webs of different weights. Tensile measurements were obtained on a Thwing Albert Tensile Tester in accordance with TAPPI Standard Number T 456m-49. Tensile was measured cross direction (CD) and machine direction (MD) for a dry strip. All tensile values are reported as ounces/inch. These values may be converted to the standard metric unit of grams per 15 millimeters by multiplying by 16.775.

EXAMPLE 1

A roll of paper having a basis weight of 30 grams per square meter and made from northern softwood kraft pulp was saturated by means of a gravure apparatus to the extent of 74% wet pick-up with a solution comprising 6% by weight, N,N'-methylenebisacrylamide and 5% potassium hydroxide. The resulting impregnated web had a consistency of 58%. After a 14-day reaction period at room temperature in sealed plastic wrap, specimens were withdrawn for evaluation. The results are shown in Table 1. Sample A is a dry sheet made from the same lot of northern softwood kraft pulp as was treated in this Example. Sample B represents Sample A after refining in a Valley beater to increase its breaking length. Sample C represents the modified pulp described in this Example and was found to contain 1.93% by weight N,N-methylenebisacrylamide. Sample D is a sheet made from a dispersion of the sheets of Samples B and C mixed in equal proportions, formed into a web and dried. It contains, of course, one-half the amount of N,N'-methylenebisacrylamide, namely 0.97% by weight.

EXAMPLE 2

Modified fiber in accordance with the present invention was produced by feeding northern softwood kraft pulp saturated to the extent of 330% wet pick-up with a solution comprising 2.9% N,N'-methylenebisacrylamide and 1.4% potassium hydroxide into a steam-jacketed high consistency continuous refiner mixing device heated to 80° C. where it resided for two minutes. The reacted pulp was collected at a consistency of 28%, diluted and acidified with phosphoric acid to pH 7 and transferred to a paper machine where the modified pulp was blended with untreated northern softwood kraft in the proportion of 50% by dry weight to all the fibers to produce towel weight webs of 41 g/m². The results are presented in Table 2.

TABLE 1

|  | Basis Weight | Breaking Length | TWA | Bulk to Basis Weight |
|---|---|---|---|---|
| A. Control | 44.0 | 2621 | 2.84 | 4.8 |
| B. Control Refined | 39.0 | 9040 | 1.92 | 4.3 |
| C. Modified Fiber | 41.0 | 945 | 5.40 | 7.1 |
| D. B/C = 1/1 Blend | 44.0 | 4114 | 3.72 | 5.2 |

TABLE 2

| | | |
|---|---|---|
| % Modified Fiber in Blend | 0 | 40 |
| Pulp Freeness (Canadian Standard) | 680 | 709 |
| Basis Weight g/m² | 40.0 | 41.0 |
| Assayed N,N'—methylenebisacrylamide % by weight of dry fiber in web | 0 | .66 |
| Physical Properties | | |
| 24-ply bulk (millimeters) | 4.6 | 4.9 |
| TWA (g/g) | 3.7 | 5.6 |
| Stretch (percent) | | |
| Machine Direction | 12.0 | 11.5 |
| Cross Direction | 1.7 | 2.7 |
| Dry Tensile | | |
| Machine Direction | 38.9 | 19.5 |
| Cross Direction | 30.3 | 16.5 |

EXAMPLE 3

Sheets of dry lap pulp (southern softwood kraft weighing 800 g/m² on an air dry basis) were uniformly impregnated with a solution at a temperature of 50° comprising 2.5% N,N'-methylenebisacrylamide and sufficient sodium hydroxide to achieve a pH of 11.5 using a gravure type applicator so as to provide a wet pick-up of 56% and a consistency of 64%. The impregnated pulp was rolled-up, enclosed in plastic film and allowed to react at room temperature for 30 days before quenching to pH 7.0 with a very dilute solution of aqueous phosphoric acid. The modified pulp contained 1.57% by weight N,N'-methylenebisacrylamide 56% of the amount applied based on nitrogen assays.

The modified pulp was blended with untreated, beaten southern softwood pulp in the proportion of 35% by dry weight to all the fibers to produce towel weight webs of approximately 50 and 40 g/m². The results are presented in Table 3 in which "basis weight" is abbreviated B.W. and "breaking length" is B.L. and "absorbency" is ABS.

The degree of refining (REFINE) by means of a Valley beater, is represented in minutes. Refining of the samples with modified pulp was used to achieve a breaking length comparable to that of the control. As may be seen, a web of comparable TWA and bulk can be achieved at a much lower basis weight by incorporation of the modified pulp of the present invention.

TABLE 3

| REFINE (min) | B.W. g/m² | BULK mm | DENSITY g/cc | BULK B.W. | MDT oz/in | CDT oz/in | B.L. m | TWA g/g | ABS. secs. |
|---|---|---|---|---|---|---|---|---|---|
| CONTROL WEB AT HIGH BASIS WEIGHT | | | | | | | | | |
| 5 | 53.2 | 5.28 | 0.516 | 6.61 | ·53.40 | 37.67 | 939.89 | 2.8 | 22.5 |
| MODIFIED PULP SUBSTITUTION IN WEB HAVING LESSER BASIS WEIGHT | | | | | | | | | |
| 7 | 49.5 | 5.59 | 0.437 | 7.54 | 32.1 | 21.9 | 595.67 | 3.7 | 6.9 |
| 15 | 43.1 | 4.64 | 0.531 | 7.20 | 46.0 | 29.2 | 950.78 | 2.9 | 30.5 |

EXAMPLE 4

60 grams of a debonded softwood kraft fluff pulp were separated into two 30 gram batts. One batt was treated with 56 grams of aqueous liquor containing 1.1 gram sodium hydroxide; and the other with 56 grams of aqueous liquor containing 1.8 grams N,N'-methylenebisacrylamide. The two batts were combined and mixed together for twenty minutes in a model N-50 HOBART institutional kitchen mixer, having a paddle which rotates within an open-topped cylindrical steel container, typically used for kneading dough. The calculated consistency was 35% and the amount of N,N'methylenebisacrylamide was 3% by weight of the total weight of the pulp. The pulp was then placed into a self-sealing plastic bag and left at 35° C. in a laboratory oven over night (16 hours). The pH was then neutralized with dilute phosphoric acid and handsheets were made from both the treated and untreated pulp. The following test data was obtained:

| | Basis Weight | TWA | Bulk to Basis Weight | Absorbency (Seconds) |
|---|---|---|---|---|
| Untreated Fluff | 49.0 | 4.97 | 5.05 | 3.5 |
| Treated Fluff | 47.9 | 8.3 | 9.93 | 0.5 |

EXAMPLE 5

Forty pounds of southern softwood kraft were slurried in 1% sodium hydroxide, then dewatered to a 50% consistency in a high pressure screw press sold under the trademark PRESSAFINER by C-E Bauer, subsidiary of Combustion Engineering, Inc., Model 560. Twenty pounds were kneaded as a aqueous control and the remaining 20 pounds kneaded with 10 pounds of neutral aqueous solution of 0.2 pounds N,N'-methylenebisacrylamide (i.e. 1% of the fiber weight) in an atmospheric double disk refiner. The calculated consistency for both was 40%. After storing both lots at ambient temperature for two weeks in separate sealed 55-gallon drums, samples of each lot were pH neutralized with dilute phosphoric acid, reslurried and made into handsheets. The following test data was obtained:

| | Basis Weight | TWA | Bulk to Basis Weight | Absorbency (Seconds) |
|---|---|---|---|---|
| Alkali Control | 35.1 | 3.59 | 5.80 | 6.5 |
| Treated | 40.8 | 8.43 | 8.20 | 1.0 |

EXAMPLE 7

To illustrate the importance of applying the N,N'-methylenebisacrylamide and alkali separately, fluff pulp fibers of the same type as in Example 4 were treated with a solution containing both N,N'-methylenebisacrylamide and sodium hydroxide. 20 pounds of pulp were slurried in water, dewatered to 50%, then kneaded in the double disc refiner with 10 pounds of an aqueous liquid containing 0.3 pounds sodium hydroxide plus 1.2 pounds N,N'-methylenebisacrylamide (6% by weight of the pulp). The calculated consistency was 40%. After storing the treated pulp at ambient temperature for two weeks in a sealed 55-gallon drum, the pH of a sample was neutralized with dilute phosphoric acid, the pulp slurried and handsheets made. The following data were obtained:

|  | Basis Weight | TWA | Bulk to Basis Weight | Absorbency (Seconds) |
|---|---|---|---|---|
| Treated | 61.6 | 8.29 | 10.2 | 0.7 |

Although the N,N'-methylenebisacrylamide dosage was six times greater in this example than in Example 5, the improvements in desirable properties were about the same.

EXAMPLE 7

Forty pounds of southern softwood kraft dry lap pulp was treated with forty pounds of a neutral aqueous solution containing 1% N,N'-methylenebisacrylamide. These damp sheets were air-dried at ambient temperatures, then fluffed in a hammermill. A 60 gram sample of this fluff was then hand-kneaded, in a self sealing plastic bag, with 170 grams of a 1% aqueous sodium hydroxide solution. The bag was sealed and left at 35° C. in a laboratory oven for 92 hours. The product was pH neutralized with dilute phosphoric acid, slurried and made into handsheets together with a sample of the dry lap. The following test data was obtained:

|  | Basis Weight | TWA | Bulk to Basis Weight | Absorbency (Seconds) |
|---|---|---|---|---|
| Control | 49.2 | 3.35 | 4.90 | 2.7 |
| Treated | 49.9 | 9.11 | 8.40 | 0.6 |

It is apparent from the foregoing Examples 4–7 that the order of chemical application is not critical to the modification reaction of the present invention.

The absorbent products of the present invention can be used in a variety of applications where absorbency is desired. In particular they are useful in applications such as feminine hygiene products, catamenial devices, disposable diapers and non-wovens for hospital and surgical use.

It is apparent that other variations and modifications may be made without departing from the present invention. Accordingly, it should be understood that the forms of the present invention described above are illustrative only and not intended to limit the scope of the invention as defined by the appended claims.

What is claimed:

1. A method for preparing modified cellulosic fibers which comprises the steps of:
   (a) applying up to 5% of N,N-methylenebiscarylamide by dry weight of said fibers;
   (b) applying an amount of alkali equivalent in alkali strength to up to ten parts sodium hydroxide to fiber by weight;
   (c) maintaining the consistency of said fibers at at least 10% so that a continuous aqueous phase around said fibers is absent and maintaining the temperature of said treated fibers below the boiling point of water throughout step (a) or (b) whichever is performed later, if performed separately or throughout steps (a) and (b) if performed simultaneously; and
   (d) excluding free radical initiators and air from the fibers treated in accordance with steps (a) and (b) until the modification reaction is complete.

2. The method of claim 1 wherein steps (a) and (b) are performed simultaneously.

3. The method of claim 2 wherein the consistency is between 20 and 45%.

4. The method of claim 1 wherein said fibers are in the form of a batt or web.

5. The method of claim 4 wherein the consistency is greater than 45%.

6. The method of claim 1 wherein said fibers are fines.

7. The method of claim 1 wherein said fibers are wood pulp fibers derived from a mechanical pulping process.

8. The product made in accordance with claim 1.

9. The product made in accordance with claim 6.

10. The product made in accordance with claim 7.

11. An improved process for delignifying pulp by ozonization wherein the ozonization stage is preceded by the method of claim 1.

* * * * *